United States Patent [19]

Yokoo et al.

[11] 4,039,577
[45] Aug. 2, 1977

[54] PROCESS FOR PREPARING PHENYLISOPROPYLUREA DERIVATIVES

[75] Inventors: Hidejiro Yokoo, Tokyo; Tetsuo Tsuruya, Yokohama; Shigehiro Chaen, Kawasaki; Hiroshi Kubo, Yokohama, all of Japan

[73] Assignee: Showa Denko K.K., Japan

[21] Appl. No.: 592,313

[22] Filed: July 1, 1975

[30] Foreign Application Priority Data

July 3, 1974  Japan .................................. 49-75441

[51] Int. Cl.² .................. C07C 127/17; C07C 127/19
[52] U.S. Cl. ............................ 260/553 A; 260/553 R; 260/553 C
[58] Field of Search ............ 260/553 A, 553 C, 553 R

[56] References Cited

U.S. PATENT DOCUMENTS

| 3,049,562 | 8/1962 | Wright, Jr. et al. ............. 260/553 A |
| 3,627,778 | 12/1971 | Nusslein et al. ............. 260/553 A X |

FOREIGN PATENT DOCUMENTS

| 756,638 | 4/1967 | Canada ........................... 260/553 A |
| 619,827 | 3/1949 | United Kingdom | |

OTHER PUBLICATIONS

Kretov et al., CA 48:9944c (1953).
Kaneyuki et al., CA 58:11268g (1961).

Primary Examiner—Daniel E. Wyman
Assistant Examiner—Thomas A. Waltz
Attorney, Agent, or Firm—Wenderoth, Lind & Ponack

[57] ABSTRACT

A process for preparing phenylisopropylurea derivatives of the formula

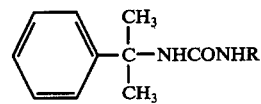
(I)

which comprises reacting a cumyl halide of the formula

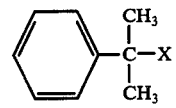
(II)

with urea or a urea derivative of the formula

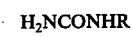
(III)

4 Claims, No Drawings

PROCESS FOR PREPARING PHENYLISOPROPYLUREA DERIVATIVES

This invention relates to a process for preparing phenylisopropylurea derivatives [i.e., N-(α, α-dimethylbenzyl)-N'-substituted or unsubstituted ureas] of the following general formula

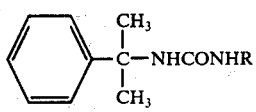
(I)

Wherein R is a hydrogen atom, a phenyl group, a phenyl group substituted by at least one alkyl group containing 1 to 4 carbon atoms, or a phenyl alkyl group.

These phenylisopropylurea derivatives are useful as herbicides and other agricultural chemicals, raw materials for preparing these agricultural chemicals, and intermediates for preparing various organic compounds. For example, compounds of formula (I) in which R is phenyl or substituted phenyl can be used effectively as herbicides. A compound of formula (I) in which R is hydrogen can be easily converted to the corresponding cumyl isocyanate by reaction with sodium nitrite in the presence of hydrogen chloride. The resulting isocyanate is used as intermediates for various organic compounds. For example, when this isocyanate is reacted with N-methylaniline, there can be obtained N-(α,α-dimethylbenzyl)-N$\zeta$- phenylurea useful as a herbicide.

Generally, urea derivatives are obtained by reacting primary or secondary amines with isocyanates. The starting isocyanates are usually prepared by reacting the corresponding amines with an excess of phosgene. The use of phosgene, however, requires a strict control in order to maintain good environment. In particular, under the current rigorous environmental control imposed on industrial plants, it is frequently difficult even to handle phosgene.

According to a very special example of preparing urea derivatives, ureas and olefins or alcohols are used as starting materials. Such a method, however, is unsuitable for preparation of phenylisopropylurea derivatives of formula (I). In fact, experiments of the inventors of the present application showed that the intended compounds could hardly be obtained.

In contrast, the present invention has the advantage that the above urea derivatives can be prepared in high yields at normal atmospheric pressure and a relatively low reaction temperature without the need to use dangerous phosgene having very high toxicity to man and domestic animals or to use a special pressure reactor.

The present invention provides a new process for preparing phenylisopropylurea derivatives of the formula

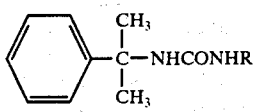
(I)

wherein R is a hydrogen atom, a phenyl group, a phenyl group substituted by at least one alkyl group containing 1 to 4 carbon atoms, or a phenyl alkyl group, which comprises reacting a cumyl halide of the formula

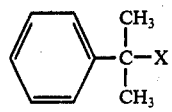
(II)

wherein X is a chlorine or bromine atom, with urea or a urea derivative of the formula

 (III)

wherein R is the same as defined above.

Peter A. S. Smith: The Chemistry of Open Chain Organic Nitrogen Compounds, Vol. 1, page 271 (W. A. Benjamin, Inc. New York, 1965) discloses that alkylating agents attack ureas on O, forming isourea salts. This means that dehydrohalogenation does not take place in a reaction between an organic halide and urea. The inventors of the present application reacted benzyl chloride with urea under such mild conditions as are employed in the present invention, and ascertained that dehydrochlorination hardly took place. In view of this, it is unexpected and surprising that when the cumyl halide of formula (II) is reacted with the urea or urea derivative of formula (III) in accordance with the present invention, the phenylisopropylurea derivatives of formula (I) are easily formed with the occurrence of dehydrohalogenation.

Specific examples of the urea derivatives of formula (I) are N(αα-dimethylbenzyl)urea, N-(α,α-dimethylbenzyl)-N'-phenylurea, N-(α,α-dimethylbenzyl)-N'-(o-, m-, or p-)tolylurea, N-(α,α-dimethylbenzyl)-N'-(2,4-dimethylphenyl)urea, N(α,α-dimethylbenzyl)-N'-benzylurea, N-(α,α-dimethylbenzyl)-N'-(α-methylbenzyl)urea, and N,N'-bis(α,α-dimethylbenzyl)urea. As is clear from the above structural formula, all of these urea derivatives have the structural characteristic that a quaternary carbon atom of the phenylisopropyl group (α,α-dimethylbenzyl group) is bonded to one nitrogen atom on which one hydrogen atom is retained, and at least one hydrogen atom is bonded to the other nitrogen atom of the urea skeleton.

The cumyl halide used as a starting material in this reaction can be prepared easily be reacting α-methylstyrene obtainable at a relatively low cost in the petrochemical industry, with a hydrogen halide. Among the compounds of formula (III), urea is readily available as an industrial product. The substituted urea compounds can be easily obtained by reacting the corresponding amines such as aniline or toluidine with sodium cyanate in an aqueous solution of hydrochloric acid. Needless to say, the reaction materials used in the process of this invention are not limited to those obtained by the above-mentioned methods, but those prepared by other synthesizing methods can also be used.

Since the cumyl halide of formula (II) is a relatively unstable compound, it is desirable to prepare it immediately before it is submitted to the process of this invention. It can also be prepared in situ during the performance of the process of this invention. For example, α-methylstyrene is reacted with a hydrogen halide to form a cumyl halide of formula (II), and subsequently, the urea compound of formula (III) is added. Or a hydrogen halide is introduced into a mixture of α-methylstyrene and the urea compound (III) with stirring, whereby the cumyl halide formed in situ is reacted with the urea compound.

The reaction in accordance with this invention can be performed in the absence of a solvent. Usually, however, it is preferred to perform it in the presence of a solvent. Suitable solvents used for this purpose are aprotic solvents. When the starting material (III) is urea, hydrocarbons may be used. But water can also be used as the solvent as an exception to the above, and this is rather preferred. When the starting material (III) is a urea derivative containing a phenyl group or an alkyl-substituted phenyl group, it is appropriate to use aprotic solvents having strong polarity. Examples of highly polar aprotic solvents which can be used especially preferably include dimethylformamide, acetonitrile, dimethylsulfoxide, nitromethane, nitrobenzene, methyl isobutyl ketone, methyl ethyl ketone and acetone. Mixtures of these highly polar aprotic solvents with small amounts of other kinds of aprotic solvent such as dioxane, tetrahydrofuran, cyclohexanone, chloroform, chlorobenzene, benzene, toluene, xylene or ether can also be used. There is no particular limit to the amount of the solvent used, and the amount can be chosen properly according to the embodiment of performing the process of this invention.

It has been found that according to this invention, very good results can be obtained by performing the above reaction in the presence of $\alpha$-methylstyrene. It is presumed that in this case, the $\alpha$-methylstyrene captures the hydrogen halide formed as a by-product and changes to the cumyl halide of formula (II), and again participates in the reaction with the urea compound of formula (III). The $\alpha$-methylstyrene may be added to the reaction mixture at the time of the reaction, or it may be present as an excessive portion left as a result of using it in excess relative to the hydrogen halide in the preparation of the starting cumyl halide. The amount of $\alpha$-methylstyrene is preferably 1 to 10 moles, more preferably 3 to 6 moles, per mole of the cumyl halide.

The reaction in accordance with this invention proceeds almost stoichiometrically, but from the standpoint of inhibiting side-reactions or improving economy and productivity, the reaction is carried out preferably by using either one of the starting materials in slight excess. Usually, it is preferred to employ the urea compound (III) in excess, for example, in an amount of more than 1 mole but up to about 5 moles per mole of the cumyl halide (II). When urea is used as the urea compound (III) and the reaction is carried out in the presence of water, the suitable amount of urea is at least 2 moles. This is because urea catches the hydrogen halide formed as a byproduct to change to a hydrogen halide salt, and this salt no longer participates in the reaction.

The reaction in accordance with this invention proceeds under relatively mild conditions. The reaction temperature is usually 0° to 100° C., preferably 10° to 80° C. There is no particular restriction on the reaction pressure, and conveniently, the reaction is carried out at atmospheric pressure. These conditions are not altogether strict, but can be varied as desired. When the temperature is too high, undesirable phenomena such as the decomposition or polymerization of the starting materials or the product or other side-reactions are likely to occur. Accordingly, heating to a temperature above 100° C. should be avoided in general. The reaction time is generally in inverse proportion to the reaction temperature. At high temperatures, it is 1 to several hours, and at low temperatures, it is 1 to 4 days.

All of the products of formula (I) are solid at room temperature, and can be recovered as crystals from the resulting products. The crystals can, if desired, be purified by known procedures such as recrystallization.

The following Examples illustrate the present invention. Needless to say, these Examples do not limit the invention in any way. All parts in these Examples are by weight.

EXAMPLE 1

A mixture of 154.5 parts of cumyl chloride and 120 parts of urea was heated with stirring, and reacted at 70° C. for 3 hours. The reaction mixture was cooled with ice, and 1000 parts of a 2N aqueous solution of sodium hydroxide was added dropwise with stirring, thereby to afford white crystals. The crystals were collected, washed with water and n-hexane, and dried to afford 139 parts of white crystals. The resulting crystals were found to contain N-($\alpha,\alpha$-dimethylbenzyl)urea (III: R=H) having a purity of 89% as a result of analysis by nmr spectrum [$\delta$1.73(6H, s); $\delta$5.91 (2H, br. s.); $\delta$6.93 (1H, br. s.); $\delta$7.1-7.7 (5H, m), 35° C., 60MC, $d_6$-pyridine solvent, 5wt.% solution, TMS reference.]. The remainder (11%) was N, N'-bis($\alpha,\alpha$-dimethylbenzyl)urea (III: R=$-$C(CH$_3$)$_2$C$_6$H$_5$) [nmr spectrum, $\delta$1.67 (12H, s) $\delta$6.42(2H, br. s.), $\delta$7.1-7.7 (10H, m), same conditions as above.]. They were separated by fractional crystallization from hydrous alcohol. The former had a melting point of 190.5 to 191° C., and the latter had a melting point of 226° to 227° C.

EXAMPLE 2

180 g (3 moles) of urea was dissolved in 100 ml. of water. The solution was heated to 55° C., and with stirring, 155 g (1 mole) of cumyl chloride was added dropwise over the course of 2 hours. After the addition, the reaction was continued for an additional 3 hours at 60° C. After cooling, the reaction product was neutralized with a 2N aqueous solution of sodium hydroxide. The resulting crystals were collected by filtration, and washed with a small amount of n-hexane and then with water, and dried in vacuo at 80° C. to afford 151 g of white crystals which were identified as N($\alpha,\alpha$-dimethyl benzyl) urea having a purity of 94%. The remainder (4%) was N,N'-bis($\alpha,\alpha$-dimethyl benzyl)urea.

EXAMPLE 3

A mixture of 15.4 (100 millimoles) of cumyl chloride, 18.0 g (300 millimoles) or urea and 30.0 g of $\alpha$-mehtylstyrene was stirred at 60° C. for 5 hours. The resulting crystals were collected by filtration, neutralized with a 1N aqueous solution of sodium hydroxide, washed with water and dried to afford 17.5 g of white crystals which were N($\alpha,\alpha$-dimethyl benzyl)urea having a purity of 98%, and contained 2% of N,N'-bis($\alpha,\alpha$-dimethyl benzyl)urea.

EXAMPLE 4

102 parts of phenylurea was suspended in 80 parts of acetonitrile, and 25.4 parts of an $\alpha$-methylstyrene solution containing 30.5% of cumyl chloride was added. With stirring, they were reacted at 40° C. for 5 hours. After allowing the reaction product to stand for 2 days, the precipitated crystals were collected and recrystallized from hydrous alcohol to afford 7.6 parts of N-phenyl-N'-($\alpha,\alpha$-dimethylbenzyl) urea (III: R=C$_6$H$_5$). The melting point of the crystals was 193 to 194° C.

EXAMPLE 5

11.3 parts of p-tolylurea was suspended in 80 parts of acetonitrile, and 7.7 parts of cumyl chloride and 24 parts of α-methylstyrene were added. With stirring, they were reacted at 40° C. for 6 hours. The reaction mixture obtained was allowed to stand for 2 days, and the precipitated crystals were collected. The crystals were washed with n-hexane, and recrystallized from 60% methanol to afford 13.8 parts of N-(α,α-dimethylbenzyl)-N'-(p-tolyl). urea (III: R=C$_6$H$_4$ -CH$_3$-p) having a melting point of 203° C.

EXAMPLE 6

12.4 parts of 2,4 -xylylurea was suspended in 50 parts of nitrobenzene, and 30 parts of α-methyl-styrene was added. The mixture was stirred while introducing anhydrous hydrobromic acid portionwise. When the amount of the mixture increased by 10 parts, the introduction of the hydrobromic acid was stopped. The reaction was then performed at 40° C. for 5 hours. The resulting reaction mixture was allowed to stand overnight. Then, 30 parts of n-hexane was added, and the mixture was further allowed to stand overnight. The precipitated crystals were recrystallized from 60% methanol to afford 13.4 parts of N-(α,α-dimethylbenzyl)-N'-(p-tolyl-)urea having a melting point of 203° C.

EXAMPLE 7

12.4 parts of 2,4-xylylurea was suspended in 50 parts of acetonitrile, and 7.7 parts of cumyl chloride and 24 parts of α-methylstyrene were added. With stirring, they were reacted at 40° C. for 6 hours. After allowing the reaction mixture to stand for one day, 50 parts of n-hexane was added. The mixture was further allowed to stand overnight. The precipitated crystals were collected, and recrystallized from 60% methanol to afford 12.5 parts of N-(α,α-dimethylbenzyl)-N'-(2,4,-xylyl) urea (III: R=—C$_6$H$_3$(CH$_3$)$_2$ —2,4) having a melting point of 163° C.

EXAMPLE 8

30 ml. of α-methylstyrene was placed in a 200 ml. reactor, and while externally cooling with ice, anhydrous hydrochloric acid was introduced at 0 to 10° C. When the weight of the mixture increased by 1.8 g, the introduction of the hydrochloric acid was stopped. 11.3 g of p-tolylurea and 40 parts of acetonitrile were added, and with stirring, the mixture was heated. After heating it for 4 hours at 40 ± 2 ° C., the reaction mixture was maintained at 20° C. for 3 days. The precipitated crystals were collected, and recrystallized from 70% methanol to afford 13.5 g of N-(α,α-dimethylbenzyl)-N'-(p-tolyl)urea having a melting point of 203° C.

EXAMPLE 9

The reaction filtrate collected in Example 8 (resulting from the removal of the crystals from the reaction mixture) was recovered, and 16 ml. of α-methylstyrene, 2 ml. of cumyl chloride, and 11.3 g of p-tolylurea were added. The mixture was reacted at 40° C. for 4 hours, and allowed to stand for 3 days. The precipitated crystals were collected, and recrystallized from 70% methanol to afford 12.8 g of N-(α,α-dimethylbenzyl)-N'-(p-tolyl)urea.

EXAMPLE 10

11.25 parts of p-tolylurea, 7.72 parts of cumyl chloride and 23.64 g of α-methylstyrene were added to 80 parts of methylisobutyl ketone, and the reaction was performed at 60° C. for 5 hours. After the reaction, the solvent was evaporated off at reduced pressure. The residue was washed with n-hexane, and recrystallized from a mixture of water and methanol to afford 5.4 parts of N-(α,α-dimethylbenzyl)-N'-(p-tolyl)urea.

EXAMPLE 11

The same procedure as in Example 7 was repeated except that the same amount of tetrahydrofuran was used instead of the methyl isobutyl ketone. There was obtained 3.4 parts of N-(α,α-dimethylbenzyl)-N'-(p-tolyl) urea.

EXAMPLE 12

7.7 parts of cumyl choloride and 13.4 parts of cumyl urea were added to a mixture of 20 parts of acetonitrile and 5 parts of tetrahydrofuran, and the mixture was heated at 50° C. for 1 hour with stirring. The reaction mixture was concentrated at reduced pressure, and the residue was recrystallized from 60% methanol to afford 8.8 parts of N,N-bis(α,α-dimethylbenzyl) urea having a melting point of 226° to 227° C.

What we claim is:

1. A process for preparing phenylisopropylurea derivatives of the formula

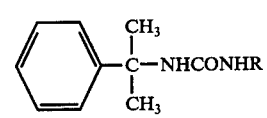

(I)

wherein R is a a phenyl group, a phenyl group substituted by at least one alkyl group containing 1 to 4 carbon atom, or a phenylalkyl group the alkyl group of which contains 1 to 3 carbon atoms
which comprises reacting, at a temperature of 10° to 80° C, a cumyl halide of the formula

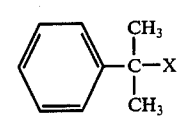

(II)

wherein X is a chlorine or bromine atom, with a urea derivative of the formula

H$_2$NCONHR          (III)

wherein R is the same as defined above, and the reaction being carried out in a solvent which consists of:
a. at least one member selected from the group consisting of dimethylformamide, acetonitrile, diemthylsulfoxide, nitromethane, nitrobenzene, methyl isobutyl ketone, methyl ethyl ketone and acetone; or
b. a mixture of a member (a) with at least one member selected from the group consisting of dioxane, tetrahydrofuran, cyclohexanone, chloroform, chlorobenzene, benzene, toluene, xylene and ether.

2. The process of claim 1 wherein a urea derivative in which R is a phenyl group, a phenyl group substituted by at least one alkyl group of 1 to 4 carbon atoms, or a phenylalkyl group, the alkyl group of which contains 1 to 3 carbon atoms, is used as said starting material of formula (III), and the reaction is carried out in the presence of α-methylstyrene.

3. The process of claim 1 wherein said reaction is carried out in the presence of 1 to 10 moles, per mole of the cumyl halide, of 60:methylstyrene.

4. The process of claim 3 wherein said reaction is carried out in the presence of 3 to 6 moles, per mole of the cumyl halide, of α-methylstyrene.

* * * * *